United States Patent
Roy et al.

(10) Patent No.: US 10,653,351 B2
(45) Date of Patent: May 19, 2020

(54) SYSTEMS AND METHODS FOR QUANTIFICATION OF POSTURAL BALANCE OF USERS IN AN AUGMENTED REALITY ENVIRONMENT

(71) Applicant: Tata Consultancy Services Limited, Mumbai (IN)

(72) Inventors: Sangheeta Roy, Kolkata (IN); Oishee Mazumder, Kolkata (IN); Debatri Chatterjee, Kolkata (IN); Kingshuk Chakravarty, Kolkata (IN); Aniruddha Sinha, Kolkata (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 16/172,668

(22) Filed: Oct. 26, 2018

(65) Prior Publication Data

US 2019/0125238 A1    May 2, 2019

(30) Foreign Application Priority Data

Oct. 28, 2017  (IN) .............................. 201721038331

(51) Int. Cl.
*A61B 5/00* (2006.01)
*A61B 5/11* (2006.01)
(Continued)

(52) U.S. Cl.
CPC .......... *A61B 5/4023* (2013.01); *A61B 5/1114* (2013.01); *A61B 5/1121* (2013.01); (Continued)

(58) Field of Classification Search
CPC combination set(s) only.
See application file for complete search history.

(56) References Cited

U.S. PATENT DOCUMENTS 9,081,436 B1 * 7/2015 Berme ..................... G01L 5/163
9,149,222 B1 * 10/2015 Zets ......................... A61B 5/16
(Continued)

FOREIGN PATENT DOCUMENTS

WO    WO-2016/038215    3/2016

OTHER PUBLICATIONS

Webster, D. et al. (2014). "Systematic review of Kinect applications in elderly care and stroke rehabilitation," *Journal of NeuroEngineering and Rehabilitation*, vol. 11, No. 108; pp. 1-24.
(Continued)

*Primary Examiner* — Michael Le
(74) *Attorney, Agent, or Firm* — Finnegan, Henderson, Farabow, Garrett & Dunner LLP

(57) ABSTRACT

Systems and methods for quantification of postural balance of users in an augmented reality (AR) environment. Traditional systems and methods provide for quantifying the postural balance using the AR environment but none of them quantify or restrict the functional tasks performed by the users to a predefined level. Embodiments of the present disclosure provide for the quantification of the postural balance with a variable step height in the AR environment by acquiring first set of information comprising of data on skeletal joints, filtering the first set of information for obtaining a filtered set of data, computing the set of postural data based upon the filtered set of data and quantifying the postural balance based upon the set of postural data by computing threshold values for obtaining postural stability index scores and determining based upon the postural stability index scores, the postural balance of the users in the AR environment.

6 Claims, 6 Drawing Sheets

(51) Int. Cl.
*G06N 5/04* (2006.01)
*G06F 17/15* (2006.01)
*G06T 19/00* (2011.01)
*G16H 50/30* (2018.01)
*G16H 20/30* (2018.01)
*G16H 50/20* (2018.01)

(52) U.S. Cl.
CPC ............ *A61B 5/1126* (2013.01); *G06F 17/15* (2013.01); *G06N 5/048* (2013.01); *G06T 19/006* (2013.01); *G16H 20/30* (2018.01); *G16H 50/20* (2018.01); *G16H 50/30* (2018.01); *A61B 5/1122* (2013.01); *A61B 5/1128* (2013.01)

(56) References Cited

U.S. PATENT DOCUMENTS

| | | | |
|---|---|---|---|
| 9,451,916 B2* | 9/2016 | Curtiss | A61B 5/6898 |
| 2010/0049095 A1* | 2/2010 | Bunn | A61B 5/1038 600/595 |
| 2013/0035613 A1* | 2/2013 | Curtiss | A61B 5/6898 600/595 |
| 2015/0050629 A1* | 2/2015 | Pease | A63B 63/00 434/247 |
| 2015/0364059 A1* | 12/2015 | Marks | G16H 20/30 482/9 |
| 2017/0000383 A1* | 1/2017 | Brown | A61B 5/1116 |
| 2017/0087416 A1* | 3/2017 | Hu | A61B 5/112 |
| 2017/0263005 A1* | 9/2017 | Takeda | G06K 9/00342 |

OTHER PUBLICATIONS

Maudsley-Barton, S. et al. (Jul. 2017). "A Comparative Study of the Clinical use of Motion Analysis from Kinect Skeleton Data," located at https://arxiv.org/pdf/1707.08813.pdf, 6 pages.

* cited by examiner

SYSTEMS AND METHODS FOR QUANTIFICATION OF POSTURAL BALANCE OF USERS IN AN AUGMENTED REALITY ENVIRONMENT

PRIORITY CLAIM

This U.S. patent application claims priority under 35 U.S.C. § 119 to: India Application No. 201721038331, filed on Oct. 28, 2017. The entire contents of the aforementioned application are incorporated herein by reference.

TECHNICAL FIELD

This disclosure relates generally to relates to quantification of postural balance of users in an augmented reality (AR) environment, and more particularly to the present disclosure relates to systems and methods for quantification of postural balance of users in the augmented reality (AR) environment.

BACKGROUND

Postural stability or balance comprises ability to maintain oneself in a correct and proper posture with an ability to prevent oneself from falling. Maintenance of the vertical body posture and its control are complex and comprises of mobility and correction processes from brain, hip, shoulders etc. Postural balance may be affected by progressive and chronic degenerative changes within the structures of nervous system that control motor function, the visual system, hearing, proprioception, and balance. Patients become prone to falls, especially during rapid head movements. Postural instability is one of the prominent symptom associated with geriatric population and in many patients with neurological disorders like Stroke, Dementia, Parkinson's disease (PD), etc. Postural instability is one of the cardinal signs of PD. The instability leads to progressive reduction in both static and dynamic balance, resulting in recurrent falls.

Quantification of the postural balance of a person is necessary to assess the person's original medical problem and their rate of progress through rehabilitation or even through tele-rehabilitation. Therefore data capture and analysis, even while completing therapeutic activities (for example during functional movement tasks) can be used to provide information to therapist(s), optimize motional limit tasks and adaptively alter feedback settings and motional task difficulty. Measurement or quantification of stability is required to estimate severity of stroke, define treatment plan and monitoring progress of rehabilitation programs.

Further, the quantification of the postural balance in virtual environments or augmented reality based systems has become a need of the modern day health care due to increasing use of artificial intelligence and robotics in the field of medicines, healthcare, radio-activities and therapy activities. Modern day health care comprises, inter-alia, providing health care based upon use of tele-medicine facilities, health based applications and performing surgeries through robots. Augmented Reality (AR) comprises superimposition of a computer-generated image on a user's view of the real world to provide a composite view. AR may be implemented using a see-through stereoscopic display or by a see-through holographic or volumetric three-dimensional display. While being part of the virtual environment, a patient (or any person) can interact within a seemingly real or physical way, to use or manipulate objects or special electronic equipment. AR based systems superimpose digital information on top of the patient's real world (natural) view of his/her surrounding environment. AR may also add sound, graphics and haptics etc. to the real world view. Further, the AR based systems can provide a real-time feedback.

The traditional systems and methods provide assessment of postural stability using the AR based systems but none of them quantify or restrict the functional tasks performed by patient to a predefined level, instead, the patients are leveraged to accomplish it according to their capability. This leads to an unreliable or inaccurate stability assessment because each time the functional task level is unintentionally altered by the same patient, such as, the rising height of one leg in single-leg stance (SLS), the stability procedures are most likely to vary from trial to trial.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

Systems and methods of the present disclosure enable quantification of postural balance in an augmented reality (AR) environment. In an embodiment of the present disclosure, there is provided a method for quantifying postural balance of users in the augmented reality (AR) environment, the method comprising: acquiring, by a sensor, a first set of information from one or more users, wherein the first set of information comprises a set of data on skeleton joints of the one or more users; filtering, using a multivariate de-noising technique, the first set of information for extracting a filtered set of data to compute a set of postural data of the one or more users, wherein the filtered set of data comprises data obtained by filtering noise from the first set of information; computing, based upon the filtered set of data, the set of postural data for quantifying the postural balance of the one or more users, wherein the set of postural data comprises data on postures and activities of the one or more users; quantifying, using a fuzzy controller in the AR environment, the postural balance of the one or more users based upon the set of postural data by: computing, by classifying the set of postural data based upon a set of rules, one or more threshold values to obtain one or more postural stability index scores; and determining, based upon the one or more postural stability index scores, the postural balance of the one or more users in the AR environment; and obtaining the one or more postural stability index scores by performing a correlation of the set of postural data with the one or more threshold values based upon the set of rules for the quantification of the postural balance of the one or more users in the AR environment.

In an embodiment of the present disclosure, there is provided a system for quantification of postural balance of users in an augmented reality (AR) environment, the system comprising one or more processors; one or more data storage devices operatively coupled to the one or more processors and configured to store instructions configured for execution by the one or more processors to: acquire, by a sensor, a first set of information from one or more users, wherein the first set of information comprises a set of data on skeleton joints of the one or more users; filter, using a multivariate de-noising technique, the first set of information for extracting a filtered set of data to compute a set of postural data of the one or more users, wherein the filtered set of data comprises data obtained by filtering noise from the first set of information; compute, based upon the filtered set of data, the set of postural data for quantifying the postural balance of the one or more users, wherein the set of postural data comprises data on postures and activities of the one or more users; quantify, using a fuzzy controller in the AR environment, the postural balance of the one or more users based upon the set of postural data by: compute, by classifying the set of postural data based upon a set of rules, one or more threshold values to obtain one or more postural stability index scores; and determine, based upon the one or more postural stability index scores, the postural balance of the one or more users in the AR environment; and obtain the one or more postural stability index scores by performing a correlation of the set of postural data with the one or more threshold values based upon the set of rules for the quantification of the postural balance of the one or more users in the AR environment.

In yet another embodiment, there is provided one or more non-transitory machine readable information storage mediums comprising one or more instructions which when executed by one or more hardware processors causes the one or more hardware processors to perform a method for system and methods for quantification of postural balance of users in an augmented reality environment, the method comprising: acquiring, by a sensor, a first set of information from one or more users, wherein the first set of information comprises a set of data on skeleton joints of the one or more users; filtering, using a multivariate de-noising technique, the first set of information for extracting a filtered set of data to compute a set of postural data of the one or more users, wherein the filtered set of data comprises data obtained by filtering noise from the first set of information; computing, based upon the filtered set of data, the set of postural data for quantifying the postural balance of the one or more users, wherein the set of postural data comprises data on postures and activities of the one or more users; and quantifying, using a fuzzy controller in the AR environment, the postural balance of the one or more users based upon the set of postural data by: computing, by classifying the set of postural data based upon a set of rules, one or more threshold values to obtain one or more postural stability index scores; and determining, based upon the one or more postural stability index scores, the postural balance of the one or more users in the AR environment; and performing a correlation of the set of postural data with the one or more threshold values based upon the set of rules for the quantification of the postural balance of the one or more users in the AR environment.

It is to be understood that both the foregoing general description and the following detailed description are exemplary and explanatory only and are not restrictive of the invention, as claimed.

BRIEF DESCRIPTION OF THE DRAWINGS

The embodiments herein will be better understood from the following detailed description with reference to the drawings, in which.

DETAILED DESCRIPTION

Figure 1:
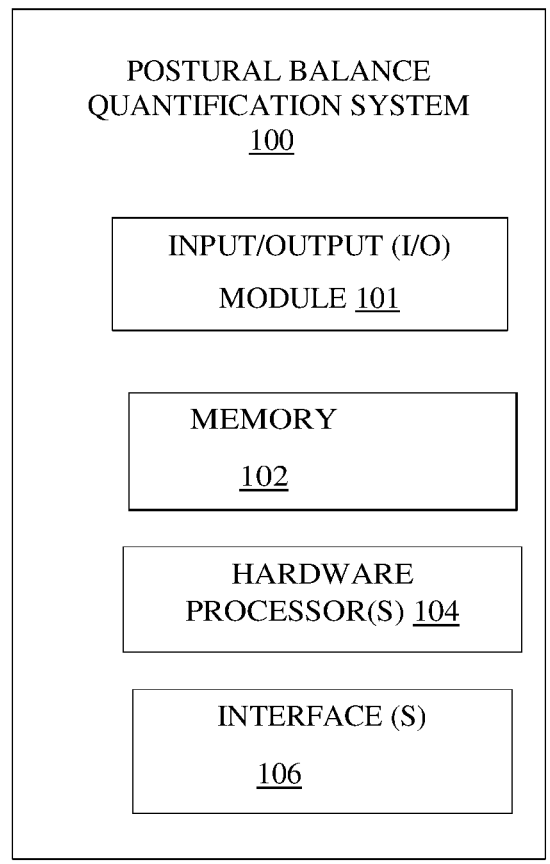
FIG. 1 illustrates a block diagram of a system for quantification of postural balance of users in an augmented reality (AR) environment, according to an embodiment of the present disclosure.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments of the present disclosure provide systems and methods for quantification of postural balance of users in an augmented reality (AR) environment. Postural instability is one of the prominent symptom associated with geriatric population and in many patients with neurological disorders like Stroke, Dementia, Parkinson's disease (PD), etc. Postural instability is also the major precursor of fall and about 35% of geriatric population fall each year, making fall prediction a significantly impacting parameter for geriatric health monitoring. Post stroke rehabilitation treatment reveals that about 83% of stroke patients suffers from postural instability leading to high fall risk. Measurement or quantification of stability is required to estimate severity of stroke, define treatment plan and monitoring progress of rehabilitation programs. Postural instability is one of the cardinal signs of PD. The instability leads to progressive reduction in both static and dynamic balance, resulting in recurrent falls.

As the healthcare facilities move towards using artificial intelligence and robotics to provide an accurate and round-the-clock facilities to patients, the AR plays an important role. The AR comprises superimposition of a computer-generated image on a user's view of the real world to provide a composite view.

The traditional systems and methods provide for assessment of postural stability using the AR environments but none of them quantify or restrict the functional tasks performed by patient to a predefined level, instead, the patients are leveraged to accomplish it according to their capability. This leads to an unreliable or inaccurate stability assessment because each time the functional task level is unintentionally altered by the same patient, such as, the rising height of one leg in single-leg stance (SLS), the stability procedures are most likely to vary from trial to trial. Hence, there is a need for a technology that provides for a stability score (or a postural stability index score) by accommodating varying functional task levels of the users (for example, lifting of a leg) in the AR environments to accurately and reliably quantify the postural balance of the users in virtual and real environments.

Referring now to the drawings, and more particularly to FIG. 1 through FIG. 6, where similar reference characters denote corresponding features consistently throughout the figures, there are shown preferred embodiments and these embodiments are described in the context of the following exemplary system and/or method.

FIG. 1 illustrates an exemplary block diagram of a postural balance quantification system 100 for quantifying the postural balance of one or more users, according to some embodiments of the present disclosure. The postural balance quantification system 100 includes an Input/Output (I/O) module 101, a Single Limb Stance (SLS) duration measurement module (not shown in the figure), a body joint vibration measurement module (not shown in the figure), a sway area determination module (not shown in the figure), a stability index generation module (not shown in the figure), and a stability assessment module (not shown in the figure).

The I/O module 101 is configured to provide at least a channel with appropriate communication protocol support, for facilitating communication between the postural balance quantification system 100 and at least one external entity. The 'external entity' herein can be a user or an external system. For example, using a suitable interface provided by the I/O module 101, one or more users may interact with the postural balance quantification system 100. In another example, an external system can connect and communicate with the postural balance quantification 100, for data transfer and/or any such action. The I/O module 101 can be further configured to provide suitable communication channel for communication between the components of the postural balance quantification system 100. The I/O module 101 is further configured to provide suitable options for monitoring action(s) being performed by one or more users, and collect one or more inputs with respect to one or more actions being performed by the user. The I/O module 101 is further configured to collect one or more inputs required for the postural balance quantification, by monitoring the user. For example, the I/O module 101 can use a Kinect® sensor that is internally or externally associated (or connected) with the postural balance quantification system 100, so as to monitor user action(s) and collect the required input(s).

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Figure 2:
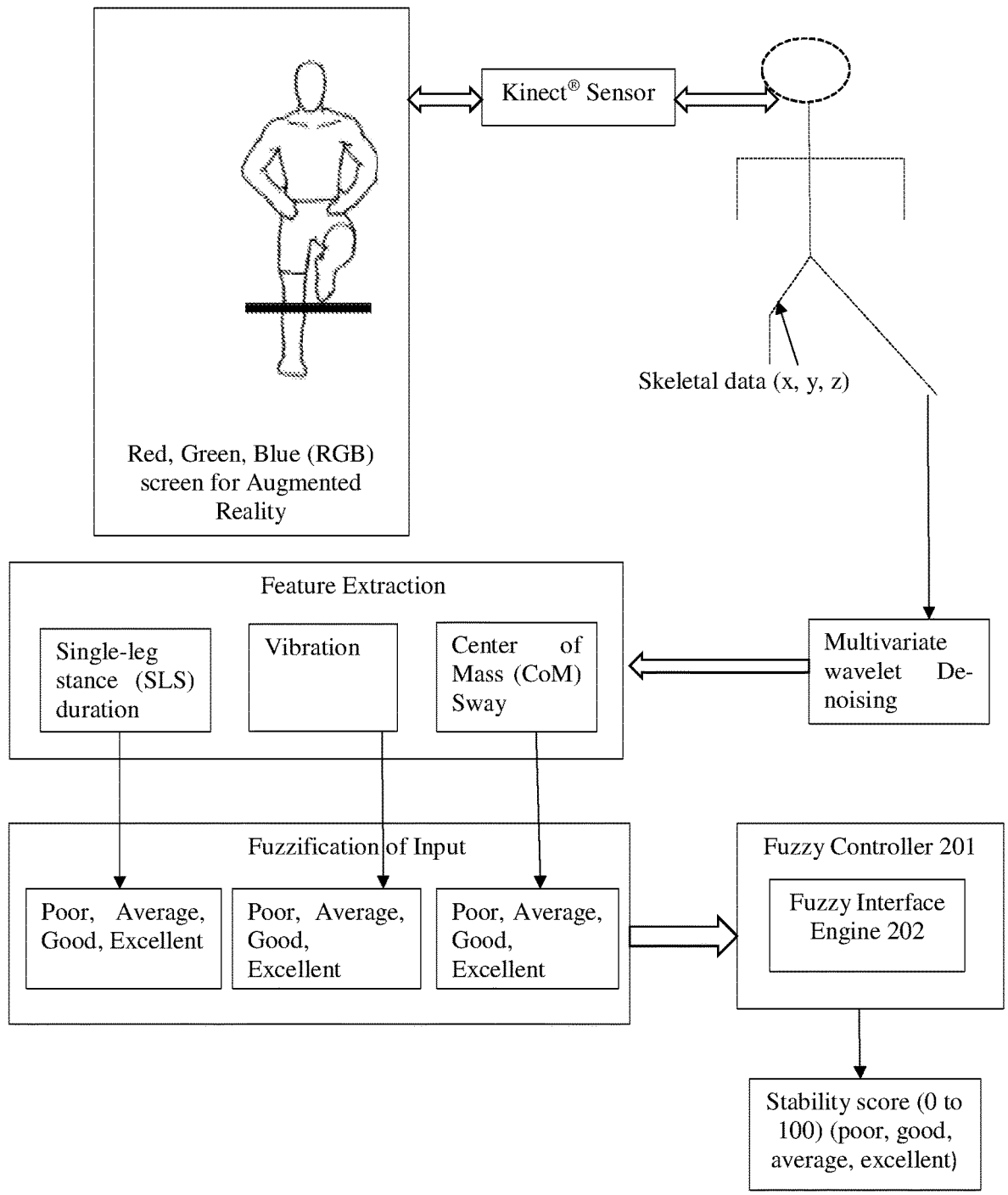
FIG. 2 is an architecture illustrating the components and flow of a system for the quantification of the postural balance of the users in the AR environment, according to an embodiment of the present disclosure.

According to an embodiment of the present disclosure, referring to FIG. 2, the architecture, flow and components of a system for quantifying the postural balance in the AR environment may be considered in detail. A Kinect® sensor provides for a skeletal data (comprising of data on skeleton joints) of one or more users performing varying degree of single-leg stance (SLS) activities in the AR environment. The skeletal data may then be filtered using multivariate de-noising technique. The multivariate de-noising technique is used for creating a multivariate statistical model where all relevant information can be estimated more accurately, and the model parameters improve more flexible. Then a high quality image can be selected by binding to the fractal space wavelet de-noising method. Various features (like vibration, CoM Sway) may then be extracted from the filtered data. A fuzzy controller 201 (comprising of a fuzzy interface engine 202) may then perform a fuzzification of information or data (for example, on the vibration or CoM Sway) by applying a set of fuzzy rules defined in the fuzzy interface engine 202. This may then be used to obtain the postural stability index score representing a quantified postural balance of the one or more users. The fuzzy controller 201 further comprises, inter-alia, of a control system working on fuzzy logic which analyzes one or more analog input values in terms of one or more logical variables and is used to perform, inter-alia, a fuzzification and/or a defuzzification for mapping mathematical input values into fuzzy membership functions. The fuzzy interface engine 202 may be used to perform fuzzy inference using the fuzzy controller 201 and may also be customized to include one or more membership functions.

Figure 3:
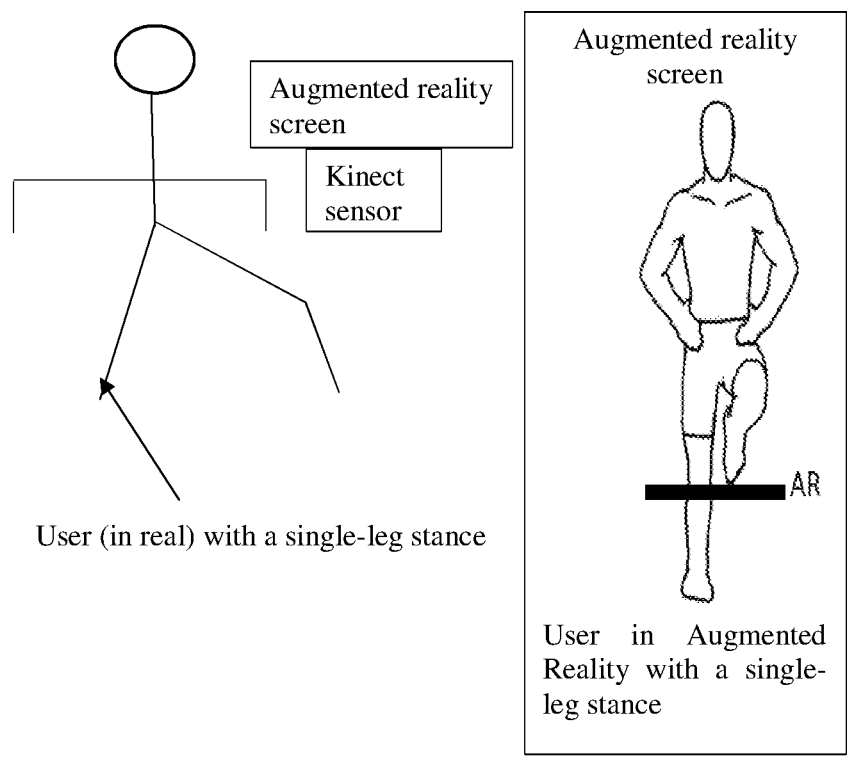
FIG. 3 illustrates a block diagram of a user with a single-leg stance in a real and the AR for the quantification of the postural balance in the AR environment, according to an embodiment of the present disclosure.
Figure 4:
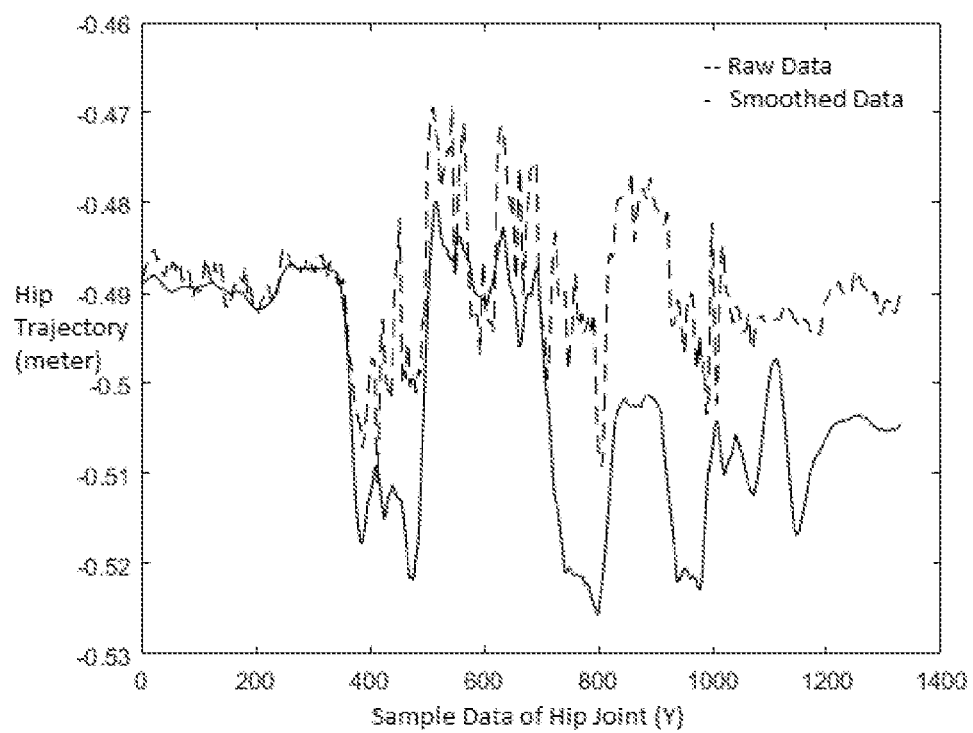
FIG. 4 shows the graphical representation of data on skeleton joints acquired and filtered for the quantification of the postural balance of the users in the AR environment, according to an embodiment of the present disclosure.

FIG. 3 illustrates a user with single-leg stance (SLS) in a real and the AR environment. The postural balance quantification system 100 provides for the quantification of the postural balance of the one or more users in the AR environment by computing a plurality of postural stability index scores based upon a single-leg stance (SLS) with variable step heights. FIG. 3 illustrates an example of one of the single-leg stances of a user in both real and the AR environment. FIG. 4 shows the graphical representation of data (comprising of skeletal data of the one or more users) acquired using the Kinect® sensor (represented by dotted lines) and then filtered using the multivariate de-noising technique (represented by non-dotted or bold lines).

Figure 5:
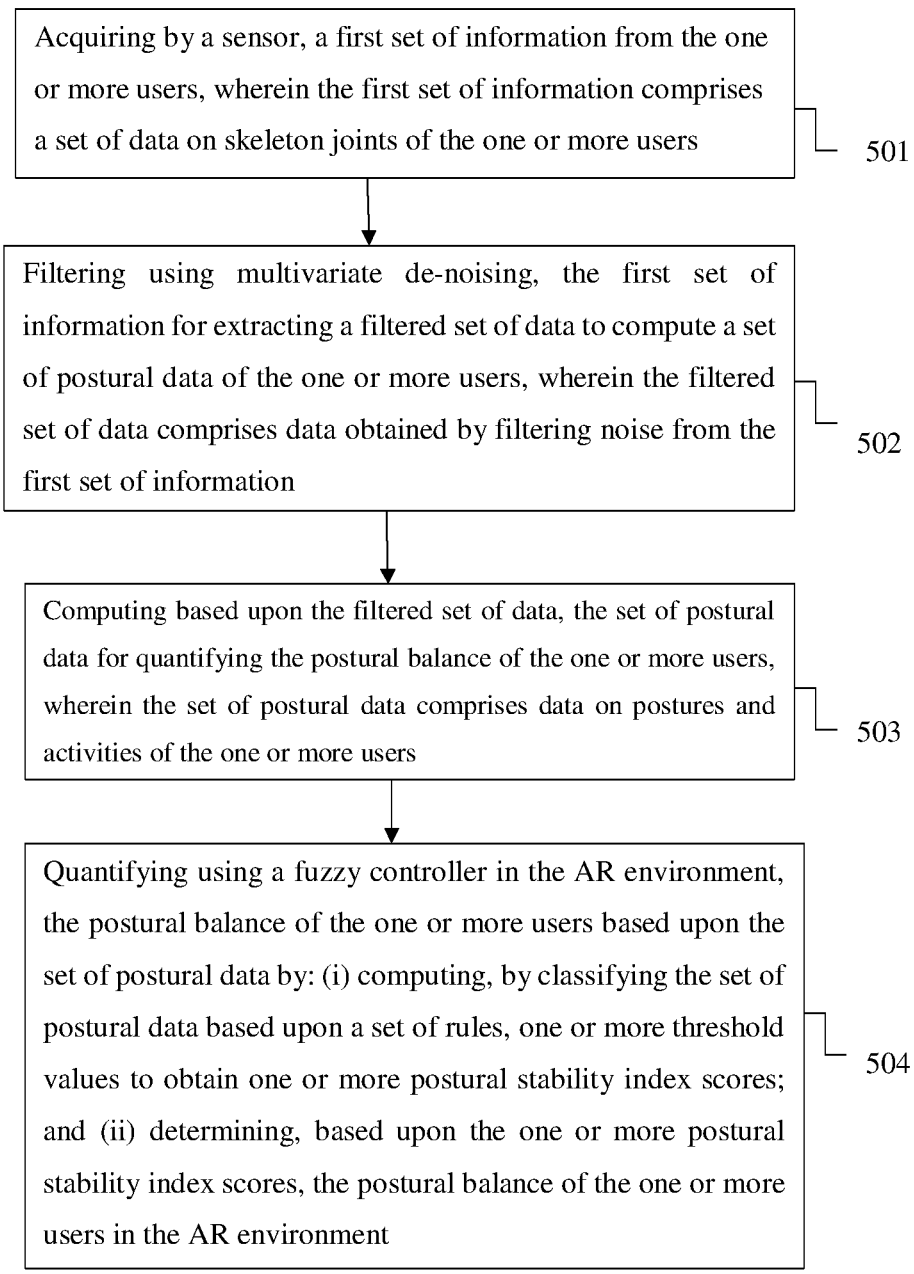
FIG. 5 is a flowchart illustrating the steps involved for the quantification of the postural balance of the users in the AR environment according to an embodiment of the present disclosure.

FIG. 5, with reference to FIGS. 1 through 4 illustrates an exemplary flow diagram of a method for the quantification of the postural balance of the one or more users in the AR environment. In an embodiment the postural balance quantification system 100 comprises one or more data storage devices of the memory 102 operatively coupled to the one or more hardware processors 104 and is configured to store instructions for execution of steps of the method by the one or more processors 104. The steps of the method of the present disclosure will now be explained with reference to the components of the postural balance quantification system 100 as depicted in FIG. 1 and the flow diagram. In the embodiments of the present disclosure, the hardware processors 104 when configured the instructions performs one or more methodologies described herein.

According to an embodiment of the present disclosure, at step 501, a first set of information from the one or more users is acquired by using a sensor. The sensor may comprise of a Kinect® sensor and the first set of information may comprise of a set of data on skeleton joints of the one or more users. The first set of information may thus comprise of three-dimensional (3D) spatio-temporal information of multiple skeleton joints of the one or more users acquired from the Kinect® sensor. For capturing the first set of information from the one or more users, the Kinect® comprises, inter-alia, of a camera (or an image capturing device).

The camera records the one or more user actions in the form of a skeleton frame pertaining to the one or more users. The Kinect® camera captures the effective line of sight to the one or more user skeletal frame data presented in real-time on the user interface, and to match the standard posture vector corresponding to the bones and bone skeletal point segment may exhibit bright green, while the posture error vector corresponding to the bones and skeletal bone segments point will be showing a bright red, while accompanied by the voice or noise prompts. For example, referring to FIG. 4, the first set of information when Kinect® is used for monitoring and data collection may be referred. The dotted lines represent the raw data comprising of the first set of information. The first set of information may comprise of the set of data on timestamps and x, y and z position of twenty-five skeleton joints obtained from the Kinect® represented by 3D world co-ordinates (x, y, z) where 'x' represents left/right variation, 'y' represents up/down variation w.r.t ground and 'z' represents to/from variation of subject w.r.t the Kinect®.

According to an embodiment of the present disclosure, at step 502, the first set of information may be filtered using the multivariate de-noising technique to extract a filtered set of data. The filtered set of data comprises data obtained by filtering noise from the first set of information acquired above for computing a set of postural data of the one or more users. The multivariate de-noising technique may comprise, inter-alia, of determining a wavelet domain noise model and a non-parametric multivariate wavelet-domain description of a signal probability density for image data. A noise corrected image is determined from the image data, image signal, wavelet-domain noise model and the non-parametric multivariate wavelet-domain description of the signal probability density function, and a Bayesian multivariate minimum mean square error (MMSE) estimation formula. The multivariate de-noising technique may thus create a multivariate statistical model where all relevant information can be estimated more accurately, and the model parameters improve more flexible. Then a high quality image can be selected by binding to the fractal space wavelet de-noising method. Finally, the predicted image fractal wavelet coding without noise from noise in the image, so as to achieve the purpose of optimizing de-noising. The multivariate de-noising technique may thus further improve the signal-to-noise ratio and reduces the mean square error signal. Referring to FIG. 4 again, the filtered set of data comprising of the data from hip-joint extracted from the first set of information denoted by non-dotted lines may be referred.

According to an embodiment of the present disclosure, at step 503, the set of postural data for quantifying the postural balance of the one or more users may be computed based upon the filtered set of data. The set of postural data is computed to quantify the postural balance of the one or more users. The set of postural data may comprise of data on postures and activities of the one or more users (for example, lifting a leg). However, for performing the computation of the set of postural data and to finally quantify the postural balance of the one or more users (explained in step 504 below) in the AR environment, the present disclosure considers quantifying a Single-leg stance (SLS) with variable step height of the one or more users for obtaining data on from SLS duration, vibration (of hip joints) and center of mass (CoM) sway.

In an embodiment, the computation of the set of postural data may comprise firstly, of designing the AR environment. The design and working of the AR environment may now be considered in detail. The present disclosure implements an adaptive AR based training task using cross platform game engine like Unity 5.5.1.f1. The AR environment may further augment Single-leg stance (SLS) functional task and may further perform a classification into three pre-defined level exercises namely, basic, intermediate and difficult. The one or more users may interact with the AR environment using a simple graphical user interface (GUI) that enables the one or more users to select different quantification levels of postural balance, monitor the duration of the activities (performed by the one or more users) and a stability index score (or a balance score). The AR environment may guide the one or more users to perform activities or tasks (for example, taking different postures) and may further engage the one or more users to hold their respective positions in a correct way by providing necessary feedback intermittently. Thus the one or more users may perform activities or tasks without any human intervention.

The AR environment may further comprise of two galleries consisting of customized pictures based on choice of the one or more users. The galleries facilitate in creating an engaging environment (for example providing e-learning or visual feedback). Further, according to an embodiment, the pictures in galleries may start changing as the one or more users start training in the SLS. In an embodiment, the clarity of the pictures may vary depending upon the one or more users balance, for example, the picture may become clearer as the one or more users become stable. If the one or more users get imbalanced, the picture may get noisy. Thus, the proposed disclosure facilitates providing a real-time visual feedback to the one or more users to engage the one or more users in performing activities or tasks in the AR environment.

According to an embodiment of the present disclosure, the procedure for obtaining the set of postural data by augmenting single-leg stance (SLS) in the AR environment may now be considered in detail. Five right handed male users having mean age of 32.2 years were considered for study. All the male users were healthy, that is without any neurological or postural disorders or any congenital diseases. The users face the Kinect® at a distance of approximately 230 centimeters. An augmented reality scene was projected on a 44 inches computer screen which may be placed at a distance of 244 centimeters from the set-up. An integration of auditory and visual feedback regarding correcting the posture of a leg and to place the leg at a proper position on the AT set-up in terms of direction may be performed thus facilitating the users to be self-directed. The users may then perform four SLS experiments, first one without the AR environment and three others in the AR environment comprising of three different AR steps heights. The users stand for a duration of 5 seconds in a double space stance, with their eyes open and hands on their slides. The users may then perform the SLS and again return in double space phase for 5 seconds. The users remain in the SLA phase for as long as they can to a maximum time limit of 120 seconds. The users may then perform the SLS experiment in the AR environment. The height of the lifted leg may then be adjusted with reference to three step heights as may be observed in the AR screen. Basic level (step height of 3.5 inch), intermediate level (step height of 6 inch) and difficult level (step height of 10 inch). In each step the users remained in SLS phase for a maximum possible time.

According to an embodiment of the present disclosure, referring to table 1 below, the set of postural data for the one or more users (based upon the filtered set of data) may be considered. As mentioned above, the set of postural data comprises data on postures and activities of the one or more users. According to an embodiment, for quantifying the postural balance of the one or more users, the set of postural data comprises data obtained by computing the SLS duration (in time), the vibration (of hip joints) and the center of mass (CoM) sway. Referring to column B in table 1 below, the SLS time duration indicates the time period for which the user being monitored performed the action(s) as required by standard SLS test. For example, the SLS time duration is determined by monitoring variation in lifted leg's ankle coordinates. For example, when the Kinect® is used for monitoring and data collection, skeleton joints obtained from the Kinect® are represented by 3D world co-ordinates (x, y, z) where 'x' represents left/right variation, 'y' represents up/down variation w.r.t ground and 'z' represents to/from variation of subject w.r.t the Kinect®. Changes in the lifted leg's ankle y-co-ordinate (say, left leg is lifted) 'YAnkleLeft' can give meaningful information about the precise timing when a subject lifts leg (here, left-leg) above the ground. Similarly right leg's movement also can be tracked. A SLS measurement module (not shown in the figure) is configured to collect the user specific input data from the I/O module 101, process the collected data, and determine SLS time duration for the user.

According to an embodiment, referring to column C in table 1 below, vibration data of hip joints may be obtained for quantifying the postural balance. A body joint vibration determination module (not shown in the figure) is configured to collect the user specific input data collected by the I/O module 101, process the collected data, and determine values that represent one or more types of body joint vibrations while the user was performing one or more specific actions as required for the postural balance quantification. For example, while the user is standing on single limb as part of SLS exercise, the user oscillates in order to maintain the balance. Body joint, especially hip joint contributes maximally to correct the effect of instability to maintain the posture. Acceleration of hip joint center in x, y, z direction is analyzed for estimating body joint vibration. Mean frequencies of the hip joint center were calculated using appropriate techniques such as Fourier transform and the relative frequency variation between each segments of SLS (i.e., double stance, single stance followed by double stance), gives a vibration index.

According to an embodiment, referring to column D in table 1 below, the CoM sway may be obtained using a sway area determination module (not shown in the figure) is configured to assess body sway from the collected input data, and determine sway of the center of mass (CoM) sway. Any suitable technique (for example, Statically Equivalent Serial Chain (SESC)) can be used by the sway area determination module 104 for determining the CoM. SESC model locates the CoM of any linkage by means of a serial chain and the links in the chain are defined by their geometric configuration and mass distribution. Shoulder center and hip center are considered as the start and end point of the serial chain respectively. Midpoint of this chain is estimated to be the body CoM, and projection of the estimated CoM is equivalent to body sway. The sway area can be calculated using any suitable algorithm. For example, a convex hull algorithm can be used. In the convex hull method triangulation of the point sets is calculated first. The points of interest are the x and z coordinates of the estimated CoM. These coordinates (x1; z1)...(xn; Zn) of the polygon are arranged in a determinant, and cross product of the determinant generates the sway area.

TABLE 1

Set of postural data

| User (A) | Single-leg stance duration (SLS) (B) | Vibration (hip joint) (C) | Center of Mass (CoM) Sway (D) |
|---|---|---|---|
| Normal SLS without AR | | | |
| User 1, 33 years, Male | 114.26 | 40.2 | 9.6 |
| User 2, 27 years, Male | 118.20 | 36.1 | 12.10 |
| User 3, 35 years, Male | 115.12 | 47.2 | 4.93 |
| User 4, 28 years, Male | 102.34 | 47.2 | 5.6 |
| User 5, 38 years, Male | 106.65 | 29.2 | 7.1 |
| Normal SLS with AR basic step | | | |
| User 1, 33 years, Male | 105.10 | 69.1 | 10.2 |
| User 2, 27 years, Male | 118.20 | 25.2 | 14.32 |
| User 3, 35 years, Male | 115.12 | 53.0 | 5.32 |
| User 4, 28 years, Male | 102.34 | 43.0 | 6.18 |
| User 5, 38 years, Male | 106.65 | 28.6 | 6.43 |
| SLS with AR intermediate step | | | |
| User 1, 33 years, Male | 87.4 | 27.1 | 11.13 |
| User 2, 27 years, Male | 101.34 | 30.1 | 24.12 |
| User 3, 35 years, Male | 93.71 | 59.0 | 11.60 |
| User 4, 28 years, Male | 95.67 | 36.1 | 12.33 |
| User 5, 38 years, Male | 97.34 | 19.3 | 9.51 |
| SLS with AR difficult step | | | |
| User 5, 33 years, Male | 62.49 | 12.4 | 16.4 |
| User 5, 27 years, Male | 76.31 | 14.3 | 32.6 |
| User 5, 35 years, Male | 50.25 | 17.6 | 28.20 |
| User 5, 28 years, Male | 83.71 | 28.1 | 14.17 |
| User 5, 38 years, Male | 72.05 | 16.4 | 19.3 |

According to an embodiment of the present disclosure, at step 504, the one or more hardware processors 104, based upon the postural set of data (obtained in table 1 above), quantifies the postural balance of the one or more users using a fuzzy controller 201 in the AR environment. The fuzzy controller 201 may be a traditional customized fuzzy logic controller designed using Mamdani fuzzy interface system (located together with a regulating memory on a common semiconductor chip and with a conventional multipurpose controller on a common semiconductor chip) comprising of a fuzzy interface engine 202 for performing the quantification of the postural balance of the one or more users. From a methodology perspective, the fuzzy controller 201 may comprise of a set of input and output membership functions (for example a membership function for temperature may be "tool-cold", "cold", "warm", "hot" "too-hot"), a set of rules (or fuzzy rules), a fuzzification method, a defuzzification method, and an inference method. Each input and output to the fuzzy controller 201 may comprise of a set of membership functions, respectively, associated with it. For this controller, the shape and number of membership functions associated with each input can be selected freely. Typical membership functions are triangular, trapezoidal, Gaussian, or singleton.

According to an embodiment of the present disclosure, the quantification of the postural balance of the one or more users in the AR environment (based upon the set of postural data) comprises computing, by classifying the set of postural data using a set of fuzzy rules, one or more threshold values to identify a minimal optimum score in the AR environment. According to an embodiment, the one or more threshold values comprises of a set of pre-defined stability values obtained by performing a classification each of the SLS time duration, the vibration (of hip joints), and the CoM sway area under different categories (wherein each category is defined in terms of range of values). Given below is an example of the one or more threshold values obtained by performing the classification:

SLS duration: Poor: 8 to 25 sec, Average: 20 to 40 sec, Good: 35-85 sec, Excellent: 80 to 120 sec.

Vibration (body or hip Joint): Poor: 0 to 5, Average: 5 to 15, Good: 15 to 35, Excellent: 30 to 50.

CoM sway area: Poor: 16 to 25; Average: 8 to 16; Good: 4 to 8; Excellent: 0 to 4.

According to an embodiment, for fuzzy rule base generation with four input variables and four membership functions each, we require 64 rules. Each of these sixty four rules are defined and a particular output state is associated with each rule. An example of set of fuzzy rules may as below:

Rule 1: IF SLS duration is EXCELLENT; AND vibration index is GOOD; AND sway area is GOOD; THEN stability is EXCELLENT (score-75 to 100)

Rule 2: IF SLS duration is Good; AND vibration index is Average; AND sway area is GOOD; THEN stability is Good (score-50 to 75)

Rule 3: IF SLS duration is AVERAGE; AND vibration index is GOOD; AND sway area is AVERAGE; THEN stability is AVERAGE (score-25 to 50)

Rule 4: IF SLS duration is POOR; AND vibration index is POOR; AND sway area is AVERAGE; THEN stability is POOR (score-0 to 25)

According to an embodiment of the present disclosure, the present disclosure facilitates the quantification of the postural balance of the one or more users by taking the SLS in four test cases, that is, a normal SLS without AR, a normal SLS with AR basic step, a SLS with AR immediate step and a SLS with AR difficult step. The present disclosure computes one or more postural stability index scores (which represents the quantified postural balance) for the one or more users by performing a correlation of the set of postural data with the one or more threshold values based upon the set of fuzzy rules, one or more postural stability index scores of the one or more user may be generated for determining the postural balance of the one or more users in the AR environment. For example, referring to table 2 below, for the user 1, the postural stability index score has been arrived at 87.6 based upon the comparison of the set of postural data and the one or more threshold values and applying the set of fuzzy rules. The one or more postural stability index scores, as determined, may then be provided as input to a stability assessment module (not shown in the figure). The stability assessment module can be configured to interpret the postural stability index score received as input, and generate appropriate suggestions/recommendations which are then provided as output to the user. In an embodiment, the interpretation of the postural stability index score is performed by the stability assessment module, on the basis of information that is statically or dynamically configured. For example, if the postural stability index score is 20, then the postural stability is POOR, and the user may be recommended appropriate medical checkup and the like. Similarly, if the postural stability index score is 80 or more, then the postural stability is GOOD, and the user may be a healthy person with no need for medical checkup and the like.

TABLE 2

| User (A) | Single-leg stance duration (SLS) (B) | Vibration (hip joint) (C) | Center of Mass (CoM) Sway (D) | Postural stability index scores (E) |
|---|---|---|---|---|
| Normal SLS without AR | | | | |
| User 1, 33 years, Male | 114.26 | 40.2 | 9.6 | 87.6 |
| User 2, 27 years, Male | 118.20 | 36.1 | 12.10 | 91.0 |
| User 3, 35 years, Male | 115.12 | 47.2 | 4.93 | 92.0 |
| User 4, 28 years, Male | 102.34 | 47.2 | 5.6 | 91.3 |
| User 5, 38 years, Male | 106.65 | 29.2 | 7.1 | 87.0 |
| Normal SLS with AR basic step | | | | |
| User 1, 33 years, Male | 105.10 | 69.1 | 10.2 | 87.3 |
| User 2, 27 years, Male | 118.20 | 25.2 | 14.32 | 87.3 |
| User 3, 35 years, Male | 115.12 | 53.0 | 5.32 | 92.7 |
| User 4, 28 years, Male | 102.34 | 43.0 | 6.18 | 91.7 |
| User 5, 38 years, Male | 106.65 | 28.6 | 6.43 | 87.0 |
| SLS with AR intermediate step | | | | |
| User 1, 33 years, Male | 87.4 | 27.1 | 11.13 | 78.3 |
| User 2, 27 years, Male | 101.34 | 30.1 | 24.12 | 83.4 |
| User 3, 35 years, Male | 93.71 | 59.0 | 11.60 | 87.0 |
| User 4, 28 years, Male | 95.67 | 36.1 | 12.33 | 87.3 |
| User 5, 38 years, Male | 97.34 | 19.3 | 9.51 | 81.0 |
| SLS with AR difficult step | | | | |
| User 5, 33 years, Male | 62.49 | 12.4 | 16.4 | 65 |
| User 5, 27 years, Male | 76.31 | 14.3 | 32.6 | 72 |
| User 5, 35 years, Male | 50.25 | 17.6 | 28.20 | 60 |
| User 5, 28 years, Male | 83.71 | 28.1 | 14.17 | 81.6 |
| User 5, 38 years, Male | 72.05 | 16.4 | 19.3 | 73 |

Figure 6:
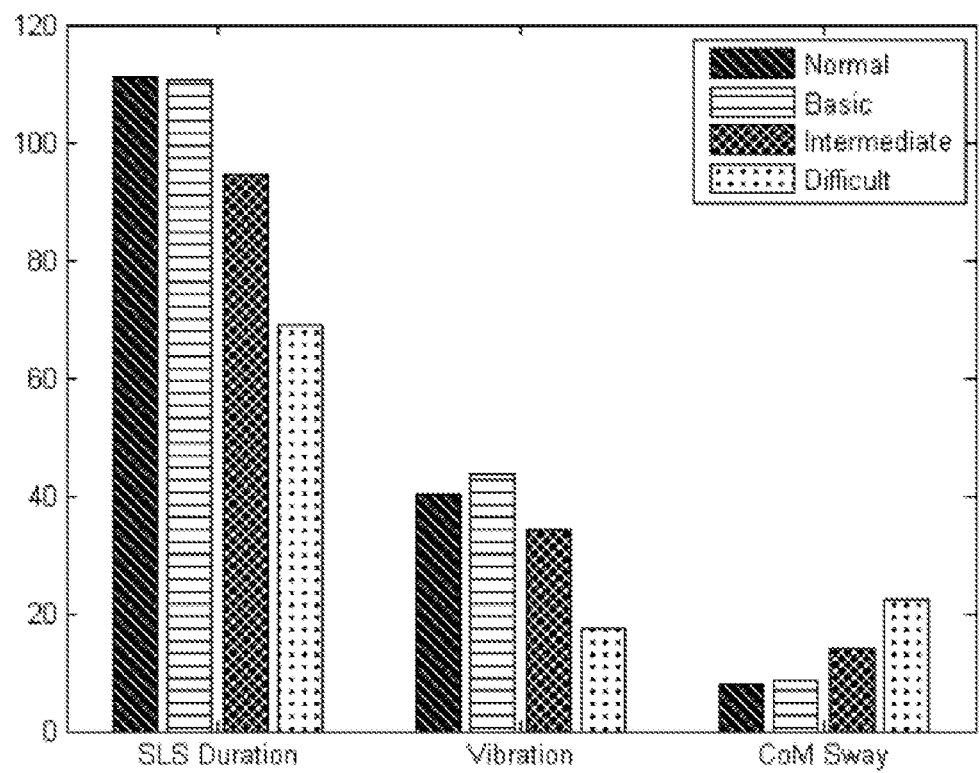
FIG. 6 shows the graphical representation of features extracted in the AR environment for the quantification of the postural balance of the users, according to an embodiment of the present disclosure.

According to an embodiment of the present disclosure, the results of the present disclosure and it's comparison with the traditional systems and methods for highlighting the importance and benefits of quantifying the postural balance in the AR environment may now be considered. Referring to table 3 above, the set of postural data acquired for the one or more users was analyzed for four test cases, namely, SLS without AR reference, SLS with AR reference in basic step height, SLS with AR reference in intermediate step height and SLS with AR reference in difficult step height. Referring to FIG. 6, average variations of feature values for the four different test cases may be referred. For normal SLS experiment, the SLS duration, the vibration (of hip joints) and the CoM Sway are high for healthy users as expected (that is 114.26, 40.2 and 9.6 respectively). According to an embodiment, the normal SLS experiment assesses only this state and as the one or more users may vary the knee flexion angle to adjust the height as per ease, only analyzing SLS in this form might not provide a detailed insight to the stability. For the second test case, that is SLS with AR reference in basic step height, the AR environment provides for a step height of 3.5 inches, which may be considered as a comfortable elevation height and referring to table 3 again, all the features values shows equivalent readings as compared to the first test case. As the step height increases, the effect of instability may become more evident and thus the SLS duration may progressively decrease when the step height increases. Similarly, the vibration (of hip joints) decreases and the CoM increases resulting in instability of the posture.

According to an embodiment of the present disclosure, based upon a comparison of the first test case and the fourth test case (where the step height is maximum), a gradation in stability features may be observed which may further indicate the need of quantifying the postural balance rather than providing for an average value. According to an embodiment of the present disclosure, referring to table 3 again, in order to validate the performance of the fuzzy stability scorer (used for obtaining the one or more postural stability index scores for the quantification of the postural balance), a comparison of the one or more postural stability index scores with Berg Balance Scale (BBS), which is a standard stability scorer may be considered. The BBS may comprise of 14 sets of questions each of which may be marked on a scale of 0 to 4 depending upon the performance of the one or more users. Thus the maximum possible score may be 56. A BBS score of (0-20) indicates high fall risk group, the score of (21-40) indicates a mid-fall risk group and the BBS score of (41-56) indicates a low fall risk group.

Referring to table 3 again, the postural feature values, the one or more postural stability index scores and the BBS score for the five users (which were under study) may be observed. It may be observed that the postural feature value along with the one or more postural stability index scores varies with the step height. However, referring to table 3 yet again, it may be observed that the BBS may always depict the same numerical stability index for the one or more users and hence the BBS may be unable to capture the variations in the postural balance due to changes in the activity level. Unlike the traditional systems and methods, the fuzzy controller 201 via a fuzzy scorer (not shown in the FIGS.) by computing the one or more postural stability index scores) incorporates all subtle changes in the postural balance. For example, referring to table 3 yet again, the one or more postural stability index scores of the user 1 may vary from a value of 87.6 to 65 depending upon the extent of the SLS activity.

Thus, the embodiments of the present disclosure facilitates implementing the postural balance quantified (or the one or more postural stability index scores) in the AR environment to be implemented in various rehabilitation programs to monitor the improvement rate of any patient or even in sports rehabilitation, where activities specific stabilities may be more critical than the gross stability estimate. This may also help a therapist to monitor the patient recovery process. Further, the present disclosure facilitates the one or more users or any therapist to regulate each training step based upon the one or more users physical ability and difficult level.

According to an embodiment of the present disclosure, the proposes the AR environment with the quantified stability may motivate, engage and guide the one or more users to perform the stability training accurately, whereas the one or more postural stability index quantified provides for a quantifiable measurement of the postural balance directly based on the conducted real time exercise. The proposed disclosure (providing for AR based rehabilitation system with the quantified postural balance in the AR environment) may also provide for tele-rehabilitation and a personalized health care based application. The proposed disclosure provides for the one or more postural stability index scores computed in real-time with a real time feedback facility to the one or more users by quantifying the SLS task with variations in step height.

In an embodiment, the memory 102 can be configured to store any data that is associated with the quantification of the postural balance. In an embodiment, the information pertaining to the first set of information, the filtered set of data, the set of postural data and the one or more postural stability index scores are stored in the memory 102. Similarly all rules that are to be used for quantifying the postural balance also are stored in the memory 102. Further, all information (inputs, outputs and so on) pertaining to the quantification of the postural balance of the one or more users may also be stored in the database, as history data, for reference purpose.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, BLU-RAYs, flash drives, disks, and any other known physical storage media.

It is intended that the disclosure and examples be considered as exemplary only, with a true scope and spirit of disclosed embodiments being indicated by the following claims.

What is claimed is:

1. A method for quantifying postural balance of users in an augmented reality (AR) environment, the method comprising a processor implemented steps of:
   acquiring, by a sensor, a first set of information from one or more users, wherein the first set of information comprises a set of data on skeleton joints of the one or more users performing various functional tasks in the AR environment;
   filtering, using a multivariate de-noising technique, the first set of information for extracting a filtered set of data to compute a set of postural data of the one or more users, wherein the filtered set of data comprises data obtained by filtering noise from the first set of information;
   computing, based upon the filtered set of data, the set of postural data for quantifying the postural balance of the one or more users, wherein the set of postural data comprises data on postures and activities of the one or more users, and wherein the computation of the set of postural data comprises augmenting Single Leg Stance (SLS) functional tasks with variations in step heights of the one or more users for computing SLS time duration, vibration of hip joints and center of mass sway area, and wherein the augmented SLS functional tasks with variations in step height are classified into various pre-defined activity levels based on the one or more users physical ability or difficulty level; and
   quantifying, using a fuzzy controller in the AR environment, the postural balance of the one or more users based upon the set of postural data by:
   computing a plurality of postural stability index scores, by performing a correlation of the set of postural data with one or more threshold values based upon a set of fuzzy rules, wherein the one or more threshold values comprises a set of pre-defined stability values obtained by performing a classification each of the SLS time duration, the vibration of hip joints and the center of mass sway area under different categories, and wherein the plurality of postural stability scores are computed for the SLS functional tasks of each pre-defined activity level in order to determine variations in postural balance due to changes in activity level; and
   providing, real-time feedback in the AR environment for correcting the posture of the one or more users by interpreting the one or more postural stability index scores computed.

2. The method of claim 1, wherein the step of obtaining the one or more postural stability index scores comprises performing a correlation of the set of postural data with the one or more threshold values based upon the set of rules for the quantification of the postural balance of the one or more users in the AR environment.

3. A system comprising:
   a memory storing instructions;
   one or more communication interfaces; and
   one or more hardware processors coupled to the memory via the one or more communication interfaces, wherein the one or more hardware processors are configured by the instructions to:
   acquire, by a sensor, a first set of information from one or more users, wherein the first set of information comprises a set of data on skeleton joints of the one or more users performing various functional tasks in an augmented reality (AR) environment;
   filter, using a multivariate de-noising technique, the first set of information for extracting a filtered set of data to compute a set of postural data of the one or more users, wherein the filtered set of data comprises data obtained by filtering noise from the first set of information;
   compute, based upon the filtered set of data, the set of postural data for quantifying the postural balance of the one or more users, wherein the set of postural data comprises data on postures and activities of the one or more users, and wherein the computation of the set of postural data comprises augmenting Single Leg Stance (SLS) functional tasks with variations in step heights of the one or more users for computing SLS time duration, vibration of hip joints and center of mass sway area, and wherein the augmented SLS functional tasks with variations in step height are classified into various pre-defined activity levels based on the one or more users physical ability or difficulty level; and quantify, using a fuzzy controller in the augmented reality (AR) environment, the postural balance of the one or more users based upon the set of postural data by:

compute a plurality of postural stability index scores, by performing a correlation of the set of postural data with one or more threshold values based upon a set of fuzzy rules, wherein the one or more threshold values comprises a set of pre-defined stability values obtained by performing a classification each of the SLS time duration, the vibration of hip joints and the center of mass sway area under different categories, wherein the plurality of postural stability scores are computed for the SLS functional tasks of each pre-defined activity level in order to determine variations in postural balance due to changes in activity level; and provide, real-time feedback in the AR environment for correcting the posture of the one or more users by interpreting the one or more postural stability index scores computed.

4. The system of claim 3, wherein the one or more hardware processors are further configured to obtain the one or more postural stability index scores by performing a correlation of the set of postural data with the one or more threshold values based upon the set of rules for the quantification of the postural balance of the one or more users in the AR environment.

5. One or more non-transitory machine readable information storage mediums comprising one or more instructions which when executed by one or more hardware processors causes the one or more hardware processor to perform a method for quantifying postural balance of users in an augmented reality (AR) environment, said method comprising:

acquiring, by a sensor, a first set of information from one or more users, wherein the first set of information comprises a set of data on skeleton joints of the one or more users performing varying functional tasks in the AR environment;

filtering, using a multivariate de-noising technique, the first set of information for extracting a filtered set of data to compute a set of postural data of the one or more users, wherein the filtered set of data comprises data obtained by filtering noise from the first set of information;

computing, based upon the filtered set of data, the set of postural data for quantifying the postural balance of the one or more users, wherein the set of postural data comprises data on postures and activities of the one or more users, and wherein the computation of the set of postural data comprises augmenting Single Leg Stance (SLS) functional tasks with variations in step heights of the one or more users for computing SLS time duration, vibration of hip joints and center of mass sway area, and wherein the augmented SLS functional tasks with variations in step height are classified into various pre-defined activity levels based on the one or more users physical ability or difficulty level; and quantifying, using a fuzzy controller in the AR environment, the postural balance of the one or more users based upon the set of postural data by:

computing, a plurality of postural stability index scores, by performing a correlation of the set of postural data with one or more threshold values based upon a set of fuzzy rules, wherein the one or more threshold values comprises a set of pre-defined stability values obtained by performing a classification each of the SLS time duration, the vibration of hip joints and the center of mass sway area under different categories, and wherein the plurality of postural stability scores are computed for the SLS functional tasks of each pre-defined activity level in order to determine variations in postural balance due to changes in activity level; and providing, real-time feedback in the AR environment for correcting the posture of the one or more users by interpreting the one or more postural stability index scores computed.

6. The one or more non-transitory machine readable information storage mediums of claim 5, wherein the step of obtaining the one or more postural stability index scores comprises performing a correlation of the set of postural data with the one or more threshold values based upon the set of rules for the quantification of the postural balance of the one or more users in the AR environment.

* * * * *